United States Patent [19]

Lostrom

[11] Patent Number: 4,464,465

[45] Date of Patent: Aug. 7, 1984

[54] CELL-DRIVEN VIRAL TRANSFER IN EUKARYOTES

[75] Inventor: Mark E. Lostrom, Redmond, Wash.

[73] Assignee: Genetic Systems Corporation, Seattle, Wash.

[21] Appl. No.: 365,218

[22] Filed: Apr. 5, 1982

[51] Int. Cl.³ .................... C12P 21/00; C12N 15/00; C12N 5/00; C12R 1/91

[52] U.S. Cl. .................................. 435/68; 435/172.1; 435/172.2; 435/240; 435/948; 424/85; 935/93; 935/71; 935/100; 935/89

[58] Field of Search ................ 435/68, 240, 241, 172, 435/172.1, 172.2, 172.3, 948; 424/85, 88

[56] References Cited

PUBLICATIONS

Yelton et al., "Monoclonal Antibodies", American Scientist, vol. 68, (1980), pp. 510–516.
Kozbor et al., "Human Hybridomas Constructed with Antigen Specific Epstein–Barr Virus–Transformed Cell Lines", Proceedings of the National Academy of Sciences 79 (1982), pp. 6651–6655.
Yeh et al., "Cell Surface Antigens of Human Melanoma Identified by Monoclonal Antibody", Proceedings of the National Academy of Sciences 76(6), (1979), pp. 2927–2931.
Schneiderman et al., "Simple Method for Decreasing the Toxicity of Polyethylene Glycol in Mammalian Cell Hybridization", Somatic Cell Genetics 5(2), (1979), pp. 263–269.
Brown et al., "Immunoglobulin Expression by Human B Lymphocytes Clonally Transformed by Epstein Barr Virus", Journal of Immunology 128(1), pp. 24–29, (1982).
Rosen et al., Nature (1977), 267:52–54.
Kozbor et al., Scand. J. Immunol. (1979), 10:187–194.
Koskimies, Scand. J. Immunol. (1979), 10:371.
Boylston et al., Scand. J. Immunol. (1980), 12:355–358.
Steinitz et al., Immunobiol. (1979), 156:41–47.
Zurawski, Jr. et al., Science (1978), 199:1439–1441.
Steinitz et al., Nature (1980), 287:443–445.
Yoshie and Ono, Cellular Immunology (1980), 56:305–316.
Croce et al., Nature (1980), 288:488–489.
Olsson and Kaplan, PNAS USA (1980), 77:5429–5431.
Bird et al., J. Exp. Med. (1981), 154:832–839.
Kozbor and Roder, Immunology (1981), 127:1275–1280.

Primary Examiner—Thomas G. Wiseman
Assistant Examiner—John E. Tarcza
Attorney, Agent, or Firm—Limbach, Limbach & Sutton

[57] ABSTRACT

Novel method, cells and compositions are provided involving transforming B-lymphocytes to provide immortalization for continuous production of monoclonal antibodies to a predetermined ligand. T-cell free B-lymphocytes are combined with an Epstein-Barr virus transformed cell sensitive to a cytotoxic agent which does not significantly affect the B-lymphocytes under conditions where the sensitive EBV transformed cell acting as the transfer agent is killed and efficiently transforms the B-lymphocyte recipient cells with EBV. The EBV transformed B-lymphocyte cells are amplified and cloned, the desired clones isolated in accordance with conventional techniques and then used for production of monoclonal antibodies.

18 Claims, No Drawings

CELL-DRIVEN VIRAL TRANSFER IN EUKARYOTES

BACKGROUND OF THE INVENTION

1. Field of the Invention

The hybridoma technique of Kohler and Milstein revolutionalized immunology and its applications to many other fields. Exquisitely specific monoclonal antibodies produced in mice and rats are available in virtually unlimited quantities. Recently, there have been reports of the production of human monoclonal antibodies. Human monoclonal antibodies have many advantages over the monoclonal antibodies developed with murine or rat systems, particularly in in vivo diagnosis and therapy. This is a particular concern with in vivo therapy, due to the risk of sensitization with xenoantisera.

Furthermore, the spectrum of the human immune response may be more restricted and therefore useful for the production of monoclonal antibodies to cell surface markers, such as HLA specificities. Also, the isolation of autoimmune monoclonal antibodies and their use as antigens could lead to human monoclonal anti-idiotypic therapy to regulate the responses to auto-antigens or transplanted tissue antigens. Finally, humoral responses to infectious disease agents could be exploited to develop useful diagnostic monoclonal antibodies. Despite these provocative advantages, the general applicability of hybridoma techniques to prepare the human monoclonal antibodies has been limited.

2. Description of the Prior Art

EBV containing supernatants have previously been utilized to transform human B cells into cell lines producing polyclonal or monoclonal antibodies against NNP hapten (Rosen et al., Nature (1977) 267:52), TPN hapten (Kozbor et al., Scand. J. Immunol. (1979) 10:187), Rh antigen (Koskimies, Scand. J. Immunol. (1979) 10:371, Boylston et al., ibid (1980) 12:355) Streptococcus A carbohydrate (Steinitz et al., Immunobiology (1979) 156:41) Tetanus toxoid (Zurawski et al., Science (1978) 199:1439), rheumatoid associated IgG (Steinitz et al., Nature (1980) 287:443) and phosphorylcholine (Yoshie and Ono, Immunol. (1980) 56:305). See also Croce et al., Nature (1980) 288:488 and Olsson and Kaplan, PNAS USA (1980) 77:5429 for reports of production of human hybridomas employing cell fusion and monoclonal antibodies from the hybridomas. See also Bird et al., J. Exp. Med. (1981) 154:832 describing EBV activation of human B lymphocytes and Kozbor and Roder, Immunology (1981) 127:1275 describing using EBV for the establishment of monoclonal antibodies against tetanus toxoid.

SUMMARY OF THE INVENTION

Method, compositions and cells are provided for the efficient formation of immortalized B-lymphocytes capable of producing monoclonal antibodies, particularly IgG. An Epstein-Barr virus (EBV) transformed mammalian cell ("transferring cell") is combined with B-lymphocytes ("recipient cells") which have been exposed to an immunogen of interest. The conditions of the combining result in the selective isolation of the immortalized recipient cells. The EBV transferring cells transfer EBV to the B-lymphocytes resulting in the immortalization of the B-lymphocytes. After amplification and cloning of the transformed B-lymphocytes under conditions providing for individual clones, the clones are screened for production of antibodies to the desired determinant site.

DESCRIPTION OF THE SPECIFIC EMBODIMENTS

Method, cells and compositions are provided which provide for the stable production of primate monoclonal antibodies. The method employs an Epstein-Barr virus ("EBV") transformed cell (normally a lymphocyte) as a transferring agent. This cell will be referred to hereafter as the "transferring cell." The transferring cell is combined or cocultivated under non-fusing conditions with cells capable of producing immunoglobulin (normally B-lymphocytes). The cells capable of immunoglobulin ("Ig") production are transformed by cocultivation with the transferring cell, becoming immortalized and committed to Ig production. The cells capable of being transformed by cocultivation and committed to immunoglobulin production will be referred to as "recipient cells." The transferring and recipient cells are cocultivated under selective conditions, whereby transformed recipient cells, which are now immortalized ("immortalized Ig producing cells"), can proliferate free of the transferring cells. These immortalized Ig producing cells may be screened for the selection of those cells producing immunoglobulin against the desired ligand specificity and subsequently cloned to establish cell lines stably producing monoclonal Ig of the desired class and isotype.

The subject method may be used for producing monoclonal antibodies of any of the immunoglobulin classes such as IgA, IgD, IgE, IgG and IgM, including the various isotypes of heavy chains e.g. $IgG_{1-4}$. Once the monoclonal antibodies have been isolated, they may be modified in a variety of ways, such as enzymatic and/or acid digestion, to produce specific fragments such as Fab, $F(ab')_2$, $F_v$, $F_d$, $F_c$, $\kappa$ and $\lambda$ light chains.

The transferring cell may be any cell which is a host for EBV and can be selected for so as to be selectively removed after transformation and immortalization of the recipient cells. Preferably the cocultivation of the transferring and recipient cells is carried out under selective cytotoxic conditions for the transferring cells. In choosing the EBV transferring cell line, to be considered are whether: It is available and can be mutated to be sensitive to a cytotoxic agent to which the recipient cells are not sensitive; it is a host for EBV and is capable of acting as a transferring cell, which upon introduction into a medium with the recipient cells, will act to transform and immortalize the recipient cells.

Cells which can be hosts to EBV are particularly humans and other primates, which includes chimpanzees, monkeys, marmosets, etc. These cells may be readily transformed with EBV in accordance with conventional ways. Various cell lines are available which contain EBV, such as human lymphoblastoid GM 4672, marmoset line B95-8, etc.

Various techniques may be employed for selectively separating the immortalized Ig producing cells to the virtual complete absence of the transferring cells. The techniques will depend to some degree on the differences between the transferring cells and the recipient cells. In some instances the cells may be separated or distinguished by their buoyant density. Various media e.g. Percoll, may be employed for providing regions of different density during centrifugation. Where the two groups of cells can be distinguished by surface antigens, antibodies, selective for the transferring cells, in conjunction with complement or lysing toxins may be useful.

For the most part, selective cytotoxic agents have found use. The selective cytotoxic agents are used where the transferring cell is sensitive to or can be sensitized to a cytotoxic agent to which the recipient cells are resistant. The sensitization can usually be achieved by subjecting the transferring cells to a mutagenic agent and then selecting for cells which are sensitive to a selective cytotoxic agent.

Various selective cytotoxic agents exist, but conveniently and commonly, the transferring cells are mutated to produce cells which are HGPRT (hypoxanthineguanine phosphoribosyltransferase) deficient, so as to be HAT (hypoxanthine aminopterin, thymidine) sensitive. Various mutation inducing agents can be employed to facilitate the derivation of HGPRT$^-$ cells, which are then sensitive to HAT. Commonly, ethyl methanesulfonate or N-nitroso guanidine is employed; see, for example, *Nature* (1975) 156:495–497.

The recipient cells, normally activated or nonactivated B-lymphocytes, may come from a wide variety of sources and hosts, with the limitation that the host must be capable of becoming an immortalized Ig producing cell. This will mean that the cell will normally be within the host range of EBV. B-lymphocytes may come from peripheral blood, tonsils, Peyer's patches, spleen and lymph nodes. The particular choice will vary depending on the purpose of the transformation. Usually the choice will depend upon the availablility of B-lymphocytes which are capable of producing a desired immunoglobulin to a determinant of interest. In other situations transforming a particular set of B-lymphocytes will be the goal.

The recipient cell may be immunized in vivo or in vitro by any desirable immunogen, either haptenic or antigenic. The determinant site of interest may be present in a simple monomeric organic compound, either naturally occuring or synthetic, polypeptides and proteins, polysaccharide, nucleic acid, or the like, or combinations thereof. The compounds may function as drugs, contaminants, pesticides, pollutants, cellular members, e.g., surface membrane proteins, cytosol proteins, nucleolus proteins, etc., enzymes, hormones, antibiotics, etc. Whole organisms or cells may be employed, such as viruses, bacteria, fungi, protozoa, mammalian cells, etc. or parts thereof, e.g. nuclei.

The B-lymphocytes may be activated by an immunogen in vivo or in vitro when producing an antibody to a ligand of interest. Hosts having undergone tonsillectomies or splenectomies can serve as sources for the particular organs. The host sources for the B-lymphocytes will be the primates, as indicated previously.

Usually, for in vivo immunization, the host will have been immunized at least once and frequently about two weeks prior to the removal of the organ. After freeing a single cell suspension of the tissue of red blood cells and granulocytes, the viable mononuclear cells are suspended in an appropriate nutrient medium and non-adherent cells separated from adherent cells.

For in vitro immunization, a source of recipient cells e.g. peripheral blood lymphocytes (PBL) may be isolated and seeded in macrophage containing nutrient medium with the appropriate antigen at a sufficient concentration to provide activation. After sufficient time for priming, generally from about 2 to 4 days, the viable cells may be separated from the dead cells and employed as recipient cells. For a description of the technique, see, for example, European Patent Application No. 44,722, filed July 16, 1981.

The transformation of the recipient cells will normally be carried out in the substantial absence of functioning viable T-cells. The removal of T-cell interference to the transformation can be achieved by either substantial removal of the T-cells or by inactivation of the T-cell.

The depletion of functional T-cells may be accomplished by any conventional means which maintains the viability of the B-lymphocyte recipient cells. Conveniently, the T-cells may be removed by formation of E-rosettes, with sheep red blood cells, which E-rosettes may then be separated from the medium. Alternatively, rather than removing the T-cells, the T-cells may be inactivated, for example, by employing cyclosporin A or other T-cell inactivating agent. Thus, the B-lymphocyte suspension which is employed should be depleted of functioning viable Tcells.

The recipient cells depleted of active T-cells and provided as a suspension in an appropriate nutrient medium may then be cocultivated with the transferring cells for transformation of the recipient cell population. The two types of cells are combined in an appropriate medium, e.g. RPMI 1640, in the substantial absence of a fusogen, generally at ratios of about 0.2–5:1 of recipient to transferring cells, usually 1–3:1. The two cell populations are cocultivated. If desired, the cells may be brought into more intimate contact by any convenient means, such as centrifugation sufficient to bring the cells into close contact without damaging the cells. Centrifugation at from about 100–200 xg at room temperature for from about 1–60 minutes is normally satisfactory, preferably at least about 5 minutes.

The cells are cocultivated and the immortalized Ig producing cells obtained free of the transferring cells by mechanical or chemical means. For the most part chemical means will be used which are selectively cytotoxic. For example, when HAT medium is used, the concentrations of the individual components will range from about $10^{-4}$ to $10^{-5}$M. The cell concentrations for each of the transferring and recipient cells will range from about $10^4$ to $10^5$ cells/ml. The temperature will generally be in the range of about 15°–40° C.

Where selective antibodies are used, the antibodies based on binding sites will be in substantial excess of the number of cells with at least sufficient amount of complement. The toxin e.g. diphtheria toxin or ricin toxin, will be joined to the antibody free of the non-specific binding portion of the toxin i.e. the B peptide.

Shortly after combining the transferring and recipient cells, the cell suspension is plated into microtiter wells. The cells are incubated under growth conditions e.g. 37° C., 6% $CO_2$ atmosphere, and maintained under selective conditions. With HGPRT$^-$ transferring cells, HAT is maintained in the nutrient medium. The immortalized Ig producing cells are found to emerge and proliferate in 7 to 14 days. The supernatants of the cells in individual wells are screened and cells in positive wells cloned under limiting dilution conditions.

The supernatant fluid of each culture microwell can be tested for immunoglobulin production by, for example, using Staphylococcus protein A in an appropriate immunoassay e.g. $^{125}$I solid phase radioimmunoassay. This technique is only diagnostic of some immunoglobulins, so that detection of other immunoglobulins may be achieved by using antibodies for Fc for the particular immunoglobulin. Cultures producing the desired immunoglobulins are cloned in an appropriate nutrient medium.

The growth of the clones may be in various media, such as nutrient media, nutrient media in combination with conditioned media, feeder layers or the like. Feeder layers include human foreskin fibroblast feeder cells, irradiated human fetal fibroblasts, lymphocyte preparations, autologous or allogeneic human PBL, mouse lymphoid cells, or the like.

After a clone which produces the desired antibody has been established, the immortalized Ig producing cells may be grown in culture flasks in an appropriate nutrient medium with conventional supplements and the antibodies harvested from the supernatant or the cells injected into the peritoneum of a host which will not reject the implant, e.g., an appropriate primate or immune system deficient host, e.g. nude mouse, and the ascites collected or the immunoglobulins in the blood harvested. Any conventional technique which provides for efficient growth of the cells and production of the immunoglobulin may be employed.

In some situations, one is not interested in producing antibodies to a known ligand, but rather determining what antibodies the host is producing for diagnostic and/or therapeutic purposes. In many situations, the antibodies produced by the host will be of interest, particularly a host having a disease, such as cancer, e.g. leukemia and lymphoma, an autoimmune disease, an infectious disease, and the like. The patient's blood or serum could be screened while the disease is manifested, during convalescence or after recovery. A source of B-lymphocytes may be taken from the host and the cells transformed in accordance with this invention to produce immortalized Ig producing cells. The Igs produced by the cells may then be screened using the appropriate antigen. In some instances it may be desirable to transform memory cells.

The immortalized Ig producing cells can be used for a number of purposes other than the direct production of antibodies to the desired determinant site. Since the cells are specific for the determinant site, they will produce large amounts of mRNA coding for the chains of the immunoglobulin. The mRNA from the cells may be isolated free of other RNA using an oligo-dT column. The presence of the desired mRNA may be established in conventional ways with oocytes. The mRNA can be used as a template for ss cDNA, which with primer and DNA polymerase will provide ds cDNA. The mixture of ds cDNA is amplified by cloning in an appropriate vector and the amplified ds cDNA screened for the presence of a sequence coding for the Fc portion of either the heavy or light chain, using a RNA or DNA probe and hybridizing under stringent conditions, according to the Southern method.

The ds cDNA coding for the desired Ig chain may be excised and modified by restriction using an appropriate endonuclease, primer repair or in vitro mutagenesis to provide a ds cDNA fragment which can be inserted into an expression vector and produce the desired amino acid sequence in a unicellular host. The light and heavy chains may be combined under renaturing conditions to produce an Ig with or without glycosidyl substituents.

The immortalized Ig producing cells may also be used as a source of the chromosome having the genes encoding the immunoglobulin. The cell may be fused with a myeloma cell to produce hybridomas capable of producing the desired immunoglobulins. Conveniently, the fusogen would be a xenogenic cell which would then produce the desired antibodies and could be introduced into a lower vertebrate, a vertebrate other than a primate.

The antibodies may be used in a variety of ways in histology, cytology, immunoassays, in vivo and in vitro diagnosis, therapy, and the like. For many purposes the antibodies will be conjugated, covalently or non-covalently, to a wide variety of materials, such as labels, particularly labels providing a signal, particles, and cells.

Labels include radionuclides, dyes, fluorescers, chemiluminescers, enzymes, substrates, cofactors, naturally occurring receptors and ligands, and the like. Particles may include magnetic particles, fluorescent particles, porous latex particles, and the like. Cells include sheep red blood cells, *S. aureus* cells, or other cell strains having a particular property or function.

In contrast to prior experience employing EBV for direct transformation of B-lymphocytes, it is found that a much higher efficiency of transformation is achieved using the transferring cells for the subject cell-driven EBV transformation and that a higher proportion of the transformed cells produced IgG, as contrasted with IgM, than has heretofore been observed.

The following examples are offered by way of illustration and not by way of limitation.

EXPERIMENTAL

Freshly drawn human peripheral blood in ACD anticoagulant (adenine-citrate-dextrose) is diluted 1:1 with sterile isotonic saline at room temperature. The diluted blood (25 ml) is overlayed on a cushion of 10 ml of Lymphocyte Separation Medium (LSM, Litton Bionetics) in sterile tubes. The tubes are centrifuged at 400 xg for 25 min at room temperature. The lymphocyte/monocyte fraction of cells is collected from the interface plus one-half the volume of LSM. The collected cells are diluted 3-fold in serum-free RPMI 1640 and pelleted at 200 xg for 10 min at room temperature. The resulting cell pellets are washed 3× in serum-free RPMI 1640 and the washed cells are counted via hemacytometer and trypan blue vital dye.

AET-SRBC (aminoethylisothiouronium bromide - sheep red blood cells) are prepared for use in T-cell depletion by E-rosetting. A mixture of 2 ml containing $1.25 \times 7$ washed PBL, 0.25 ml AET-SRBC (10% suspension) 50:1 ratio, and 2.25 ml RPMI 1640–15% fetal calf serum (FCS) is prepared and centrifuged at 200 xg for 5 min at 4° C. After incubating undisturbed for 2 hrs at 4° C., the pellet is gently resuspended, underlayed with approximately 2 ml LSM per tube at 4° C. and centrifuged at 400 xg for 20 min at 4° C. The resulting T-cell depleted PBL (E$^-$PBL) is collected at the interface. The E$^-$PBL is washed 3x in serum-free RPMI 1640 at room temperature and the cells are then counted by means of a hemacytometer and trypan blue vital dye.

The human lymphoblastoid cell line GM 1500 (Human Genetic Mutant Cell Repository, Camden, N.J.) is cultured for 24 hrs in medium containing 300 μg/ml of ethyl methansulfonate (Sigma Co.). Following the mutagensis with ethyl methansulfonate, the surviving cells are subcultured into increasing concentrations of the purine analog, 6-thioguanine (6TG). After several months, a vigourously growing mutant cell line is established which dies in HAT supplemented medium and is designated as 1A2. The cloned cell line 1A2 has been deposited at the ATCC on March 26, 1982 with accession no. CRL-8119.

The 1A2 cells are harvested from log phased cultures and washed once in serum-free RPMI 1640. The E−PBL and 1A2 cells are mixed in a 2:1 ratio and pelleted at 160 xg for 5 min at room temperature. The cell pellet is resuspended in RPMI 1640–15% FCS, 1mM sodium pyruvate, 2 mM L-glutamine and HAT (H-$1\times10^{-4}$M; A-$1\times10^{-5}$M, T-$4\times10^{-5}$M) at 37° C. The final subconcentrations are $4\times10^5$ cells/ml for E−PBL and $2\times10^5$ cells/ml for 1A2. Aliquots of 200 µl are introduced into wells of a 96 well microtitre plate and incubated at 37° C., 6% carbon dioxide and fed every other day with the RPMI 1640-HAT medium described immediately above. After about 10–14 days, the cell lines emerge and proliferate.

The clonal lines were found to contain the normal diploid number, 46 chromosomes. The cells had human surface immunoglobulin as detected by immunofluorescence, using a fluorescein-conjugated F(ab')$_2$ anti-human Ig. The cells were also found to contain Epstein-Barr nuclear antigen (EBNA) as does the 1A2 cell line.

Supernatants of transformed B-cell cultures from randomly selected wells were evaluated for the presence of immunoglobulin by precipitation and sodium dodecylsulfatepolyacrylamide gel electrophoresis (SDS-PAGE). All supernatants which were tested contained one or more human monoclonal immunoglobulins. Both IgG and IgM production were noted. In repeated experiments, using different PBL's the results were reproduced. IgG secretion was observed from a majority of ramdonly tested wells. SDS-PAGE analyses of supernatants derived from cloned B-cell lines demonstrated that each produced only one monoclonal immunoglobulin.

Since $8\times10^4$ E−PBL were plated per well, the yield of transformants for co-cultivation is reproducibly greater than one per 80,000. (Subsequent results have shown yields of one per 10,000 or better.) While all clonal supernatants contain monoclonal immunoglobulin, the amount of immunoglobulin varied among daughter clones derived from a single primary well.

A radioimmunoassay specific for the human gamma chain was used to measure the IgG content of supernatant fluids from 48 hour log phase cultures and four day higher density cultures of clonal B-lines. Between 50–350 ng/ml IgG were produced at 48 hrs, while higher density cultures of the same cells produced up to 8 µg/ml. Over four months of culture and reassay, the cloned transformants did not demonstrate any change in the quantity or class of secreted immunoglobulins.

When compared to the properties of supernatant-initiated EBV transformation of human B-cells, the subject cell-driven process has a number of demonstrated advantages. First, the rate of emergence of the transformants is faster. With 12 independent experiments using the 1A2 cell line and 12 different normal PBL donors, in each instance, the newly generated transformants grew to 75% confluency in 10–14 days. In addition, the observed efficiency of cell-driven transformation is substantially higher. From SDS-PAGE analysis and subsequent cloning studies, it was calculated that an average of 200 transformed lines were generated per $8\times10^6$ E−PBL, i.e. up to 1 B cell line per 40,000 E−PBL. Since monocytes were not depleted, the efficiency in these experiments may be an increment greater. Furthermore, using the 1A2 cell-driven method of EBV transformation, an average of 60% of the clones produced monoclonal IgG. In work by Brown and Miller, J. of Imm. (1982) 128:24, employing 100-fold concentrated EBV-containing supernatant for transforming normal adult PBL, in three trials, 16% of the clones recovered produced IgG.

It is evident from the above results, that a powerful new technique is provided for producing stable sources of monoclonal antibodies to a predetermined ligand or determinant site.

The subject method provides a number of advantages over prior art methods. By transforming with EBV, stable immortalized cells are obtained. The resulting immortalized Ig producing cells do not regress or slough off genes encoding the immunoglobulin of interest. There is no possibility with the subject immortalized Ig producing cells of producing immunoglobulins having a chain from each parent or being contaminated with a chain from the myeloma parent as has been experienced with hybridomas. The subject cells provide long term stable production of the desired immunoglobulin.

As contrasted with the use of EBV for transformation, the subject method is much more efficient in the number of recipient cells which are transformed. It is therefore feasible to use the subject method as a screen of a patient's B-lymphocyte repertoire, particularly where the immune system has been primed due to the presence of a tumor or pathogen or due to an autoimmune disease. Also, as compared to earlier results with EBV transformation, a high percentage of the immortalized Ig producing cells produce IgG, rather than IgM. Since IgM generally has a lower affinity for its homologous ligand than IgG, for many purposes IgM is not useful.

The subject method is simple, reproducible, safe and efficient and can be used with any cell capable of producing Ig from a host for EBV.

Although the foregoing invention has been described in some detail by way of illustration and example for purposes of clarity of understanding, it will be obvious that certain changes and modifications may be practiced within the scope of the appended claims.

What is claimed is:

1. A method for immortalizing recipient immunoglobulin producing cells employing an EBV transformed cell as the transferring cell, said method comprising:
co-cultivating said transferring and said recipient cells in the substantial absence of functional T-cells, for sufficient incubation times and conditions to transfer EBV to said recipient cells to produce immortalized Ig producing cells which are EBNA-positive and which have a normal diploid number of chromosomes and cloning said immortalized Ig producing cells in the virtual absence of said transferring cells.

2. A method according to claim 1, wherein at least one of said cocultivating and cloning is in the presence of a cytotoxic agent selective for said transferring cells.

3. A method according to claim 2, wherein said transferring cells are HAT sensitive and said cytotoxic selective agent is HAT.

4. A method according to claim 1, wherein said recipient cells are primed with a ligand prior to said cocultivation.

5. A method according to claim 1, wherein said recipient cells are from a host having a disease which stimulates a B-cell immune response.

6. A method for producing immunoglobulins ("Ig") specific for a predetermined determinant site, said method comprising:

co-cultivating under selectively cytotoxic conditions EBV-transformed cells sensitive to said selective conditions, as transferring cells, and B-lymphocytes activated by an immunogen containing said determinant site, as recipient cells, for sufficient incubation times and conditions, resulting in the transformation of said recipient cells to produce immortalized Ig producing cells which are EBNA-positive and which have a normal diploid number of chromosomes, and the mortality of said sensitive cells;

expanding the resulting population of immortalized Ig producing cells in an appropriate nutrient medium in individual wells and selecting for production of the desired immunoglobulin from the resulting clones; and harvesting the desired immunoglobulin from supernatants from the desired clones.

7. A method according to claim 6, wherein said selective conditions are HAT medium.

8. A method according to any one of claims 6 or 7, wherein said clones producing said desired immunoglobulin are injected into the peritoneum of a host capable of accepting said clone to produce antibody containing ascitic fluid; and said ascitic fluid is harvested.

9. A method according to any one of claims 6 or 7, wherein said clones producing said desired immunoglobulin are injected into a host capable of accepting said clone, and including the additional step of extracting said immunoglobulin from the blood of said host.

10. A method according to any one of claims 6 or 7, wherein said immunoglobulin is IgG.

11. A method according to any one of claims 6 or 7, wherein said immunoglobulin is IgM.

12. A method according to any one of claims 6 or 7, wherein said immunoglobulin is IgA.

13. A method according to any one of claims 6 or 7, wherein said immunoglobulin is IgE.

14. A method according to any one of claims 6 or 7, wherein said immunoglobulin is IgD.

15. A method for producing immunoglobulin ("Ig") specific for a predetermined determinant site, said method comprising:

co-cultivating in HAT selective conditions HGPRT-deficient EBV-transformed cells as transferring cells and B-lymphocytes activated by an immunogen containing said determinant site as recipient cells for sufficient incubation times and conditions, resulting in the transformation of said recipient cells to immortalized Ig producing cells which are EBNA-positive and which have the normal diploid number of chromosomes, and the mortality of said HGPRT-deficient cells;

growing resulting viable cells in HAT medium under limiting dilution conditions and selecting for clones producing immunoglobulin specific for said determinant site; and expanding selected clones and isolating said immunoglobulin secreted by said clones.

16. A method according to claim 15, wherein said transferring cell is 1A2 (CRL 8119).

17. A method according to claim 15, wherein said immunoglobulin is IgG.

18. A human EBV transformed cell designated 1A2 (CRL 8119).

* * * * *